United States Patent [19]
Orsolini et al.

[11] Patent Number: 5,445,832
[45] Date of Patent: Aug. 29, 1995

[54] PROCESS FOR THE PREPARATION OF MICROSPHERES MADE OF A BIODEGRADABLE POLYMERIC MATERIAL

[75] Inventors: Piero Orsolini; Frédéric Heimgartner, both of Martigny, Switzerland

[73] Assignee: Debio Recherche Pharmaceutique S.A., Martigny, Switzerland

[21] Appl. No.: 915,478

[22] Filed: Jul. 16, 1992

[30] Foreign Application Priority Data

Jul. 22, 1991 [CH] Switzerland .................. 02178/91

[51] Int. Cl.⁶ .................................... A61K 38/00
[52] U.S. Cl. .................... 424/491; 424/489; 424/490; 424/497; 424/499; 514/2; 514/16; 514/15; 514/12
[58] Field of Search .............. 424/489, 499, 501; 514/2, 15–16, 772.6

[56] References Cited

U.S. PATENT DOCUMENTS

| | | | |
|---|---|---|---|
| 4,010,125 | 3/1977 | Schally et al. | 260/8 |
| 4,622,244 | 11/1986 | Lapka et al. | 427/213.32 |
| 4,675,189 | 6/1987 | Kent et al. | 424/490 |
| 4,767,628 | 8/1988 | Hutchison | 424/426 |
| 4,954,298 | 9/1990 | Yamamoto | 264/4.6 |
| 5,192,741 | 3/1993 | Orsilini | 514/4 |

FOREIGN PATENT DOCUMENTS

| | | | |
|---|---|---|---|
| 52510 | 6/1982 | European Pat. Off. | A61K 9/50 |
| 58481 | 8/1982 | European Pat. Off. | A61K 37/02 |
| 204476 | 12/1986 | European Pat. Off. | A61K 9/00 |
| 0211267 | 2/1987 | European Pat. Off. | A61K 37/02 |
| 251476 | 1/1988 | European Pat. Off. | A61K 9/22 |
| 302582 | 2/1989 | European Pat. Off. | A61K 9/54 |

OTHER PUBLICATIONS

Chang, "Biodegradable Semipermeable Microcapsules Containing Enzymes, Hormones, Vaccines and Other Biologicals", J. Bioeng. 1 (1976) p. 25.
Langer, "Controlled Release of Macromolecules", Chemtech Feb. 1982 pp. 98–105.
Hutchison et al., "Biodegradable Carriers for the Sustained Release of Polypeptides", TIBTECH Apr. 1987 (vol. 5) pp. 102–106.
Chemical Abstracts, vol. 107, No. 13, Abstract 109765g (1987).

*Primary Examiner*—Jill Warden
*Assistant Examiner*—David Lukton
*Attorney, Agent, or Firm*—Pennie & Edmonds

[57] ABSTRACT

The process is aimed at providing a composition designed for the sustained and controlled release of medicamentous peptide substances, obtained in the form of microspheres of a biodegradable polymeric material incorporating said medicamentous substance.

It consists in converting first a water-soluble peptide or peptide salt into a water-insoluble peptide, respectively peptide salt. The following steps include preparing an organic-aqueous emulsion and then extracting the organic solvent in an excess of aqueous medium.

7 Claims, No Drawings

PROCESS FOR THE PREPARATION OF MICROSPHERES MADE OF A BIODEGRADABLE POLYMERIC MATERIAL

FIELD OF THE INVENTION

A process for the preparation of a composition designed for the sustained and controlled release of medicamentous peptide substances, obtained in the form of microspheres of a biodegradable polymeric material incorporating said medicamentous substance.

SUMMARY OF THE INVENTION

The process is aimed at providing a composition designed for the sustained and controlled release of medicamentous peptide substances, obtained in the form of microspheres of a biodegradable polymeric material incorporating said medicamentous substance.

It consists firstly in converting a water-soluble peptide or peptide salt into a water-insoluble peptide salt, then suspending said peptide salt in a solution of a biodegradable polymeric material, converting said suspension into an oil-in-water type emulsion, and finally isolating the microspheres of biodegradable polymer after transfer of the oil-in-water emulsion into an excess of an aqueous medium.

STATE OF THE ART

Various solutions have been proposed to this day for the preparation of compositions capable of a sustained and a controlled release of medicamentous substances, making use of the manufacture of biodegradable implants, of microencapsulation or of the preparation of biodegradable porous matrices obtained for example as microspheres or microparticles of various dimensions. In this respect, one can mention EP-A-0052510 for microencapsulation by phase separation of water-soluble drugs and EP-A-0058481 or U.S. Pat. No. 3976071 for the preparation of implants or of biodegradable porous matrices, based mainly on polylactide or on copolylactide-glycolide. These techniques make use of a prior dissolution in an organic solvent of the biodegradable polymer or copolymer used as support and, if required, the dissolution of the medicamentous substance itself.

Other techniques, also capable of yielding microcapsules or microspheres, make use of emulsification procedures, the most important step of such procedures being the obtention of an oil-in-water type emulsion from an organic solution of polymeric material and an aqueous solution of the peptide—see in this respect U.S. Pat. Nos. 4384975, 3891570, 4389330, 3737337, 4652441 or WO-90/13361. In any case however, those versed in the art are obliged to develop techniques which are complex and difficult to control, in order to reduce as much as possible the losses of the highly water-soluble active peptide substances, such as for example a double emulsification.

THE INVENTION

In a process using the formation of an emulsion of the oil-in-water type followed by its transfer into an aqueous medium, the invention enables, against all expectations, to overcome advantageously the shortcommings of techniques known to this day.

Actually, by firstly proceeding to the conversion of a water-soluble peptide or peptide derivative into a water-insoluble peptide salt, the invention makes available to those versed in the art, quite a novel means of taking advantage of the relative solubilities of the ingredients which are used and in particular of the solvents and "non-solvents" involved.

PREFERRED EMBODIMENTS OF THE INVENTION

More particularly, the object of the invention is a process which is characterized by the fact that:

a. a water-soluble peptide or peptide salt is converted into a water-insoluble peptide salt;

b. said water-insoluble peptide salt is suspended in an organic medium containing the biodegradable polymeric material in the dissolved state;

c. said organic suspension is dispersed in an aqueous medium forming the continuous phase of the resulting emulsion;

d. said emulsion is transferred into an excess of an aqueous medium, and finally the microspheres thus obtained are separated from the liquid phase.

In the invention, "medicamentous peptide substance", is used to designate primarily a natural or a synthetic polypeptide, which is physiologically active and which comprises from 3 to 45 amino acids. The range of polypeptides which can be treated in accordance with the process of the invention is quite extensive and includes in particular oxytocin, vasopressin, corticotrophin, calcitonin, epidermal growth factor (EGF), prolactin, inhibitin, interferon, somatostatin, insulin, glucagon, auricular natriuretic factor (ANF), endorphin, a renin inhibitor, luteinizing hormone-releasing hormone (LHRH), growth hormone releasing hormone (GHRH), peptide T or one of their synthetic analogues or homologues.

Preferably, one can mention polypeptides such as LHRH or somatostatin, or one of their synthetic homologues or analogues, such as

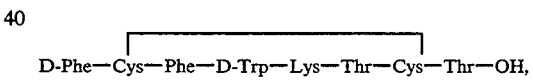

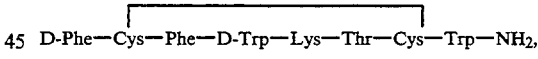

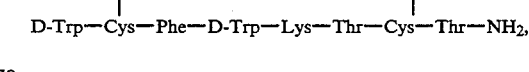

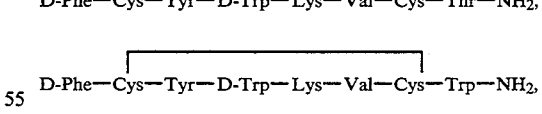

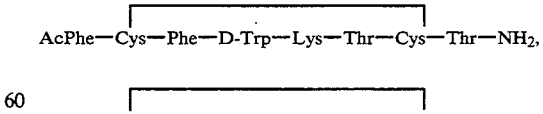

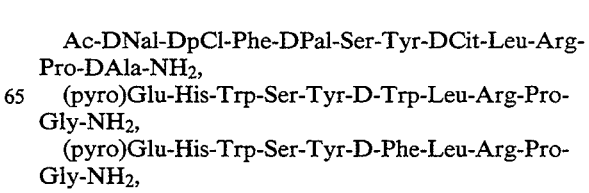

Ac-DNal-DpCl-Phe-DPal-Ser-Tyr-DCit-Leu-Arg-Pro-DAla-NH₂, (pyro)Glu-His-Trp-Ser-Tyr-D-Trp-Leu-Arg-Pro-Gly-NH₂, (pyro)Glu-His-Trp-Ser-Tyr-D-Phe-Leu-Arg-Pro-Gly-NH₂, (pyro)Glu-His-Trp-D-Ser-Tyr-D-Leu-Leu-Arg-Pro-Gly-NHR$^1$, or (pyro)Glu-His-Trp-Ser-Tyr-D-Trp-Leu-Arg-Pro-NHR$^1$, (R$^1$ = lower alkyl).

This list is however not exhaustive.

The first phase of the process consists in converting, by means of conventional techniques, a water-soluble peptide or peptide salt into a water-insoluble peptide salt. By "water-soluble" is meant a peptide or a peptide derivative having a water solubility in excess or equal to 0.1 mg/ml at 25° C., preferably in excess or equal to 1.0 mg/ml.

By "water-insoluble" is meant a peptide derivative having a water solubility lesser or equal to 0.1 mg/ml at 25° C. Peptide salts such as pamoate, tannate, stearate or palmitate satisfy this definition.

As to the biodegradable polymeric material, the most commonly used are polymers such as a polylactide, a polyglycolide, a copolymer of lactic and glycolic acids, a polyester such as a polyalkylene fumarate or succinate or further a polyorthoester, a polyacetal or a polyanhydride.

Amongst the preferred polymeric materials, one should mention the copolymers of lactic and glycolic acids (PLGA) and in particular the copolymers of L- or D,L-lactic acid containing from 45 to 90% (molar) of lactic acid units and respectively 55 to 10% (molar) of glycolic acid units.

One can also mention in this respect various polyalkylene fumarates or succinates, and in particular the poly-1,4-butylene-succinate, the poly-2,3-butylene succinate, the poly-1,4-butylene fumarate or the poly-2,3-butylene fumarate. These polymers are readily prepared as described in the literature or can be obtained from specialized firms.

As to the solvent selected for the polymeric material, one can use an organic solvent such as for example methylene chloride, but in any case, the solvent must be a "non solvent" for the selected peptide salt.

According to the invention, once said peptide salt is suspended in the organic solution of the polymeric material, this solution is incorporated into a predetermined amount of an aqueous medium, most generally of water complemented with an appropriate surfactant. The objective is to form rapidly a homogeneous emulsion of the oil-in-water type, said aqueous medium functioning to provide the continuous phase. Various factors are to be considered when preparing such an emulsion, which in turn influence the size or the structure of the microspheres resulting from the process. One of the factors which must be taken into consideration is the rate of addition of the organic solution to the aqueous medium; another one can be the temperature further the agitation speed or the energy of dispersion (ultrasonic treatment), with the last mentioned parameter influencing in particular the size of the final microspheres. It is within the capacity of those versed in the art to select the methods and the conditions of emulsification suitable for achieving the intended purpose.

In the preparation of said emulsion, it may also prove advantageous to modify the volume ratio of the phases in contact, in particular to decrease the initial volume of the organic phase with respect to that of the aqueous phase. In some cases, owing to the volatility of the organic solvents which are used—for example methylene chloride—the evaporation occurring spontaneously during agitation may already prove sufficient; in other cases, this desirable phenomenon may be accelerated by proceeding to a partial evaporation, under reduced pressure.

Once the organic-aqueous emulsion has been stabilized, it is transferred into an excess amount of an aqueous medium, most generally water. The purpose of this operation is to intensify the hardening of the embryonic microspheres formed in the emulsion, by extracting the organic solvent still remaining inside said microspheres. This operation is also aimed at eliminating at the same time trace amounts of surfactant which may have remained in the body of the polymer during its final hardening phase. It is to be noted, that water is a "non-solvent" for both the biodegradable polymeric material such as PLGA for example and for the peptide salt trapped inside said microspheres. This situation is particularly favourable for the indispensable extraction of the residual polymer solvent, such as for example $CH_2Cl_2$.

Having transferred said emulsion into an excess of an aqueous medium, the hardened microspheres are collected using conventional techniques, for example by centrifugation, filtration or by gravity settling. The same applies to the washing, purification and drying operations.

One of the advantages of the process of the invention is that it makes it possible to obtain microspheres the size of which can be accurately controlled, this control taking place mainly during the preparation of the emulsion (agitation speed for example). Another advantage is that a particularly high peptide loading can be achieved, amounting to 5, 10 or 20% in weight, or even higher, depending on conditions. Further, the yield of the peptide salt incorporation is particularly high; this is due mainly to the prior conversion of the selected peptide from a water-soluble derivative into a water-insoluble salt derivative.

The microspheres obtained according to the process of the invention from the above-mentioned ingredients are then used after being appropriately sterilized, for the preparation of suspensions used in parenteral administration, for example by intramuscular or subcutaneous injection.

The invention is illustrated by the following examples. The substances and the operational conditions used in these examples do not limit the invention in any way.

EXAMPLE 1

3 g of the acetate of D-Trp6-LHRH of the formula: (pyro)Glu-His-Trp-Ser-Tyr-D-Trp-Leu-Arg-Pro-Gly-NH$_2$ were converted into the corresponding pamoate, using conventional techniques. After comminution, this salt appears as formed of microparticles of an amorphous structure with an average particle size of approximately 10 microns. Solubility: lesser than 0.025 mg/ml in H$_2$O at 40° C.

0.280 g of the pamoate of D-Trp$^6$-LHRH were then suspended in 20 ml of $CH_2Cl_2$, and said suspension was added to 20 ml of $CH_2Cl_2$ containing 1.720 g of dissolved copolymer of D,L-lactic and glycolic acids (PLGA) 75:25 (molar %/inherent viscosity of 0.82 in HFIP). The mixture was prepared at room temperature, under stirring, to obtain a suspension which was perfectly homogeneous.

The resulting suspension was then poured, in one portion, into 500 ml of water containing 0.075% dissolved methoxycellulose and stirring of the mixture was continued for about 90 min. at room temperature (speed of agitation: 900 rpm). The evolution of the emulsion was monitored at regular intervals of time, on the average every 30 minutes, by taking a sample and examining the microspheres obtained with a microscope.

Once the stirring is ended (stabilization of the size reduction of the microspheres), said emulsion is transferred in one portion into 2 l of water maintained at approximately 10° C., while stirring the mixture until homogenization.

The microspheres of PLGA were isolated from the reaction mixture and purified by successive centrifugations alternating with washings with $H_2O$, and finally filtered and dried under reduced pressure. 1.25 g of PLGA microspheres were thus collected (yield: 63%), which included more than 96% particles having a diameter lesser than 100 microns (maximum at 55–85 microns).

The analysis (dissolution of the solid PLGA, extraction and determination of the peptide by HPLC) shows that the loading of the pamoate of D-Trp[6]-LHRH of the microspheres amounts to 9.05% in weight (theoretical: 10%).

The microspheres thus obtained were subsequently subjected to a sterilization by gamma rays and suspended in an appropriate sterile vehicle. In vivo tests (determination of the blood testosterone level in male rats) confirmed the regular release of the active substance over at least 21 days, producing from D4 (injection at D0) a collapse of the testosterone level to values typical of castrated animals.

| TIME (days) | TESTOSTERONE (ng/ml) |
|---|---|
| 0 | 3.7 |
| 2 | 5.1 |
| 4 | 0.7 |
| 7 | 0.6 |
| 11 | 0.8 |
| 14 | 1.2 |
| 18 | 1.9 |
| 21 | 2.0 |
| 25 | 2.0 |

EXAMPLE 2

Exactly the same procedure was used as in Example 1, except that 0.560 g of the pamoate of D-Trp[6]-LHRH were used for 1.440 g of PLGA 75:25 (molar %).

1.49 g of PLGA microspheres were collected (yield: 75%) and they included more than 90% particles having a diameter lesser than 100 microns.

Level of loading: 16.3% in weight (theoretical: 20%).

EXAMPLE 3

The same procedure was used as in Example 1, starting with 0.140 g of the pamoate of D-Trp[6]-LHRH and 0.860 g of poly-1,4-butylene succinate (inherent viscosity in HFIP, approximately 0.35).

The resulting organic-aqueous emulsion was transferred in one portion into 500 ml of water and the resulting mixture was subjected to successive centrifugation and $H_2O$ washing treatments, filtration and finally drying under reduced pressure to produce 0.52 g (yield: 52%) of polysuccinate microspheres.

Level of loading: 2.87% in weight (theoretical: 10%).

EXAMPLE 4

Firstly, the acetate of an analogue of somatostatine of the formula:

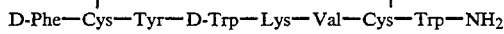

D-Phe—Cys—Tyr—D-Trp—Lys—Val—Cys—Trp—$NH_2$ was converted into the corresponding pamoate using conventional techniques, to obtain particles having an average size of approximatively 10 microns.

0.266 g of said pamoate and 1.734 g of PLGA 75:25 (molar %) were then used according to the procedure of Example 1. After pouring the organic-aqueous emulsion into 2 l of $H_2O$ at 10° C., homogenization, centrifugation and the same subsequent treatments as described above, 1.23 g (yield: 62%) of PLGA microspheres were collected, which included more than 98% particles having a diameter lesser than 100 microns (maximum at 40–65 microns).

Level of loading: 8.7% in weight (theoretical: 10%).

EXAMPLE 5

Exactly the same procedure was used as in Example 4, with 0.532 g of the pamoate of the somatostatin analogue, for 1.468 g of PLGA 75:25.

Microspheres of PLGA: 1.21 g (yield: 60%).

Level of loading: 17.5% in weight (theoretical: 20%).

The microspheres thus obtained, sterilized by means of gamma rays, were finally suspended in an appropriate sterile vehicle. In vivo tests (determination of the blood serum level of the somatostatine analogue in rats which had received one injection at JO) confirm a controlled release of a detectable amount of active substance over a period of 20 days (injection: IM).

| TIME (days) | DETERMINATION OF PEPTIDE (ng/ml) |
|---|---|
| 0 + 3 hours | 64.0 |
| 1 | 15.0 |
| 2 | 10.0 |
| 3 | 5.0 |
| 6 | 3.0 |
| 8 | 2.0 |
| 10 | 2.0 |
| 14 | 1.5 |
| 16 | 1.5 |
| 20 | 1.5 |

EXAMPLE 6

3 g of the acetate of a LHRH analogue of the formula:
Ac-D-Nal-D-pCl-Phe-D-Pal-Ser-Tyr-D-Cit-Leu-Arg-Pro-D-Ala$NH_2$ were converted into the corresponding pamoate by conventional techniques and treated in such a manner as to obtain particles having an average size of approximately 10 microns.

0.317 g of said pamoate and 1.683 g of PLGA 75:25 (molar %) were subsequently treated according to the procedure of Example 1, to produce finally 1.61 g (yield: 80%) of PLGA microspheres including more than 94% particles having a diameter lesser than 100 microns (maximum at 55–85 microns).

Level of loading: 9.05% in weight (theoretical: 10%).

EXAMPLE 7

Exactly the same procedure was used as in Example 6, with 0.634 g of the pamoate of the LHRH analogue, for 1.366 g of PLGA 75:25.

PLGA microspheres: 1.70 g (yield: 85%).
Level of loading: 18.3% (theoretical: 20%)

The microspheres thus obtained were subsequently subjected to a gamma ray sterilization and suspended in an appropriate sterile vehicle. In vivo tests (determination of the blood serum level of the analogue in male rats) confirm the regular release of a biologically significative amount of active substance over at least 24 days.

| TIME (days) | DETERMINATION OF PEPTIDE (ng/ml) |
| --- | --- |
| 0 + 3 hours | 47.1 |
| 1 | 48.9 |
| 2 | 52.2 |
| 3 | 46.9 |
| 6 | 50.4 |
| 8 | 40.1 |
| 10 | 42.1 |
| 14 | 29.8 |
| 16 | 33.5 |
| 20 | 33.0 |
| 24 | 25.6 |

These results are further confirmed by analyses carried out on subjects sacrificed at D30: loss of weight of the testes of at least 80%, loss of weight of the seminal vesicles of at least 90%.

EXAMPLE 8

Exactly the same procedure was used as in Example 1, starting with 0.05 g of the pamoate of salmon calcitonin and 1.0 g of copolymer of D,L-lactic/glycolic acids 50:50 (molar %).

The conventional in vivo tests confirm a controlled release of the active substance over a period of approximately 8 days.

---

SEQUENCE LISTING ( 1 ) GENERAL INFORMATION ( i i i ) NUMBER OF SEQUENCES: 12

( 2 ) INFORMATION FOR SEQ ID NO:1

( i ) SEQUENCE CHARACTERISTICS
( A ) LENGTH: 8
( B ) TYPE: amino acid
( C ) STRANDEDNESS: single
( D ) TOPOLOGY: circular ( i i ) MOLECULE TYPE: Peptide ( i i i ) HYPOTHETICAL: No ( x i ) SEQUENCE DESCRIPTION: SEQ ID NO: 1

```
Phe Cys Phe Trp Lys Thr Cys Trp
 1               5
```

( linkage at positions 2 and 7 )

( 2 ) INFORMATION FOR SEQ ID NO:2

( i ) SEQUENCE CHARACTERISTICS
( A ) LENGTH: 8
( B ) TYPE: amino acid
( C ) STRANDEDNESS: single
( D ) TOPOLOGY: circular ( i i ) MOLECULE TYPE: Peptide ( i i i ) HYPOTHETICAL: no ( x i ) SEQUENCE DESCRIPTION: SEQ ID NO:2

```
Trp Cys Phe Trp Lys Thr Cys Thr
 1               5
```

( linkage at positions 2 and 7 )

( 2 ) INFORMATION FOR SEQ ID NO:3

( i ) SEQUENCE CHARACTERISTICS
( A ) LENGTH: 8
( B ) TYPE: amino acid
( C ) STRANDEDNESS: single (D) TOPOLOGY: circular (ii) MOLECULE TYPE: peptide (iii) HYPOTHETICAL: no (xi) SEQUENCE DESCRIPTION: SEQ ID NO:3

Phe  Cys  Tyr  Trp  Lys  Val  Cys  Thr
       1                      5

(linkage at positions 2 and 7)

(2) INFORMATION FOR SEQ ID NO:4

(i) SEQUENCE CHARACTERISTICS
        (A) LENGTH: 8
        (B) TYPE: amino acid
        (C) STRANDEDNESS: single
        (D) TOPOLOGY: circular (ii) MOLECULE TYPE: peptide (iii) HYPOTHETICAL: no (xi) SEQUENCE DESCRIPTION: SEQ ID NO:4

Phe  Cys  Tyr  Trp  Lys  Val  Cys  Trp
       1                      5

(linkage at positions 2 and 7)

(2) INFORMATION FOR SEQUENCE ID NO:5

(i) SEQUENCE CHARACTERISTICS
        (A) LENGTH: 8
        (B) TYPE: amino acid
        (C) STRANDEDNESS: single
        (D) TOPOLOGY: circular (ii) MOLECULE TYPE: peptide (iii) HYPOTHETICAL: no (xi) SEQUENCE DESCRIPTION: SEQ ID NO:5

Phe  Cys  Phe  Trp  Lys  Thr  Cys  Thr
       1                      5

(Phe at position 1 = AcPhe;
       linkage at positions 2 and 7)

(2) INFORMATION FOR SEQUENCE ID NO:6

(i) SEQUENCE CHARACTERISTICS
        (A) LENGTH: 8
        (B) TYPE: amino acid
        (C) STRANDEDNESS: single
        (D) TOPOLOGY: circular (ii) MOLECULE TYPE: peptide (iii) HYPOTHETICAL: no (xi) SEQUENCE DESCRIPTION: SEQ ID NO: 6

Phe  Cys  Tyr  Trp  Lys  Val  Cys  Trp
       1                      5

(Phe at position 1 = AcPhe)
       linkage at positions 2 and 7)

(2) INFORMATION FOR SEQUENCE ID NO:7

(i) SEQUENCE CHARACTERISTICS
        (A) LENGTH: 11
        (B) TYPE: amino acid
        (C) STRANDEDNESS: single
        (D) TOPOLOGY: linear ( i i ) MOLECULE TYPE: peptide ( i i i ) HYPOTHETICAL: no ( x i ) SEQUENCE DESCRIPTION: SEQ ID NO:7

Xaa  Xaa  Phe  Xaa  Ser  Tyr  Xaa  Leu  Arg  Pro  Ala
    1                     5                          10

( 2 ) INFORMATION FOR SEQUENCE ID NO:8

( i ) SEQUENCE CHARACTERISTICS
        ( A ) LENGTH: 10
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: no ( x i ) SEQUENCE DESCRIPTION: SEQ ID NO:8

Glu  His  Trp  Ser  Tyr  Trp  Leu  Arg  Pro  Gly
    1                     5                          10

( 2 ) INFORMATION FOR SEQUENCE ID NO:9

( i ) SEQUENCE CHARACTERISTICS
        ( A ) LENGTH: 10
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: no ( x i ) SEQUENCE DESCRIPTION: SEQ ID NO:9

Glu  His  Trp  Ser  Tyr  Phe  Leu  Arg  Pro  Gly
    1                     5                          10

( 2 ) INFORMATION FOR SEQUENCE ID NO:10

( i ) SEQUENCE CHARACTERISTICS
        ( A ) LENGTH: 10
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: no ( x i ) SEQUENCE DESCRIPTION: SEQ ID NO:10

Glu  His  Trp  Ser  Tyr  Leu  Leu  Arg  Pro  Gly
    1                     5                          10

(Terminal amine = NHR1, R1 = lower alkyl)

( 2 ) INFORMATION FOR SEQUENCE ID NO:11

( i ) SEQUENCE CHARACTERISTICS
        ( A ) LENGTH: 9
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: no ( x i ) SEQUENCE DESCRIPTION: SEQ ID NO:11

Glu  His  Trp  Ser  Tyr  Trp  Leu  Arg  Pro

```
               1                 5
   (Terminal amine  =  NHR1,   R1  =  lower alkyl)
```

( 2 ) INFORMATION FOR SEQUENCE ID NO:12

( i ) SEQUENCE CHARACTERISTICS
        ( A ) LENGTH: 8
        ( B ) TYPE: amino acid
        ( C ) STRANDEDNESS: single
        ( D ) TOPOLOGY: circular ( i i ) MOLECULE TYPE: peptide ( i i i ) HYPOTHETICAL: no ( x i ) SEQUENCE DESCRIPTION: SEQ ID NO:12

```
        Phe  Cys  Phe  Trp  Lys  Thr  Cys  Thr
        1                  5

(Terminal amine replaced by hydroxyl group;
    linkage at positions 2 and 7)
```

What we claim is:

1. A process for preparing a composition for the sustained and controlled release of a medicamentous peptide substance, said medicamentous peptide substance being a natural or synthetic poly peptide comprising from about 3 to about 45 amino acids, said composition being obtained in the form of microspheres of a biodegradable polymeric organic material incorporating said medicamentous substance, comprising the steps of:
    (a) converting a water soluble peptide or peptide salt into a corresponding water-insoluble peptide salt selected from the group consisting of the pamoate, stearate, and palmitate of said peptide;
    (b) suspending said water-insoluble peptide salt in an organic solvent containing a dissolved biodegradable polymeric organic material to form a suspension;
    (c) dispersing said organic suspension in an aqueous medium to form an aqueous emulsion, where the aqueous medium forms the continuous phase of the emulsion;
    (d) transferring said emulsion into an excess of an aqueous medium, and separating microspheres from the liquid phase.

2. A process according to claim 1 wherein before transferring said emulsion into an excess of aqueous medium, a partial evaporation of organic medium is carried out.

3. A process according to one of claims 1 or 2, wherein the medicamentous substance is selected from the group consisting of oxytocin, vasopressin, corticotrophin, calcitonin, epidermal growth factor (EGF), prolactin, inhibitin, interferon, somatoststin, insulin, glucagon, auricular natriuretic factor (ANF), endorphin, a renin inhibitor, luteinizing hormone-releasing hormone (LHRH), growth hormone releasing hormone (GHRH), peptide T, their synthetic analogues and their synthetic homologues.

4. A process according to one of claims 1 or 2 wherein the medicamentous substance is selected from the group consisting of LHRH, somatostatin, one of their synthetic analogues or homologues,

```
     ┌─────────────────────────────┐
D-Phe─Cys─Phe─D-Trp─Lys─Thr─Cys─Thr─OH,

┌─────────────────────────────┐
D-Phe─Cys─Phe─D-Trp─Lys─Thr─Cys─Trp─NH2,

┌─────────────────────────────┐
D-Trp─Cys─Phe─D-Trp─Lys─Thr─Cys─Thr─NH2,

┌─────────────────────────────┐
D-Phe─Cys─Tyr─D-Trp─Lys─Val─Cys─Thr─NH2,

┌─────────────────────────────┐
D-Phe─Cys─Tyr─D-Trp─Lys─Val─Cys─Trp─NH2,

┌─────────────────────────────┐
AcPhe─Cys─Phe─D-Trp─Lys─Thr─Cys─Thr─NH2,

┌─────────────────────────────┐
AcPhe─Cys─Tyr─D-Trp─Lys─Val─Cys─Trp─NH2,
```

Ac-DNal-DpCl-Phe-DPal-Ser-Tyr-DCit-Leu-Arg-Pro-DAla-NH2, (pyro) Glu-His-Trp-Ser-Tyr-D-Trp-Leu-Arg-Pro-Gly-NH2, (pyro) Glu-His-Trp-Ser-Tyr-D-Phe-Leu-Arg-Pro-Gly-NH2, (pyro) Glu-His-Trp-D-Ser-Tyr-D-Leu-Leu-Arg-Pro-Gly-NHR$^1$ and (pyro) Glu-His-Trp-Ser-Tyr-D-Leu-Leu-Arg-Pro-Gly-NHR$^1$, (R$^1$=lower alkyl).

5. A process according to one of claims 1 or 2 wherein the biodegradable polymeric material is selected from the group consisting of polylactides, polyglycolides, copolymers of lactic and glycolic acids, polyesters, polyalkylene fumarate, polyalkylene succinate, polyorthoesters, polyacetals and polyanhydrides.

6. A process according to claim 5 wherein the polymeric material is a copolymer of lactic and glycolic acids, wherein the molar ratio of lactic to glycolic residues, respectively, ranges from 45:55 to 90:10, and wherein the lactic acid residues may be in either the L or D, L configuration.

7. A process according to claim 6, wherein the polyalkylene fumarate or polyalkylene succinate is selected from the group consisting of poly-1,4-butylene—succinates, poly-2,3-butylene succinates poly-1,4-butylene fumarates and poly-2,3-butylene fumarates.

\* \* \* \* \*